(12) United States Patent
Silber (10) Patent No.: US 8,131,335 B2
(45) Date of Patent: Mar. 6, 2012

(54) MULTI-CONDUCTOR CONNECTION DEVICE FOR A MEDICAL SENSOR

(75) Inventor: Daniel A. Silber, Lexington, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1187 days.

(21) Appl. No.: 11/814,408

(22) PCT Filed: Dec. 30, 2005

(86) PCT No.: PCT/IB2005/054431
§ 371 (c)(1),
(2), (4) Date: Jul. 20, 2007

(87) PCT Pub. No.: WO2006/079888
PCT Pub. Date: Aug. 3, 2006

(65) Prior Publication Data
US 2009/0292192 A1    Nov. 26, 2009

Related U.S. Application Data

(60) Provisional application No. 60/648,819, filed on Jan. 31, 2005.

(51) Int. Cl.
*A61B 5/0408* (2006.01)
(52) U.S. Cl. ........................................ 600/393; 600/506
(58) Field of Classification Search .................. 600/393, 600/506
See application file for complete search history.

(56) References Cited

U.S. PATENT DOCUMENTS

| | | | |
|---|---|---|---|
| 1,769,090 A | 7/1930 | Wappler et al. | |
| 3,871,359 A * | 3/1975 | Pacela | 600/547 |
| 3,882,851 A * | 5/1975 | Sigworth | 600/506 |
| 4,353,372 A | 10/1982 | Ayer | |
| 4,583,551 A | 4/1986 | Pike | |
| 4,733,670 A * | 3/1988 | Hays et al. | 600/506 |
| 5,341,806 A * | 8/1994 | Gadsby et al. | 600/393 |
| 5,402,780 A | 4/1995 | Faasse | |
| 5,724,984 A | 3/1998 | Arnold et al. | |
| 5,938,597 A | 8/1999 | Stratbucker | |
| 5,947,897 A | 9/1999 | Otake | |
| 6,032,064 A | 2/2000 | Devlin et al. | |
| 6,456,872 B1 * | 9/2002 | Faisandier | 600/523 |
| 2005/0070808 A1 * | 3/2005 | Marks et al. | 600/507 |
| 2005/0177062 A1 * | 8/2005 | Skrabal et al. | 600/547 |

FOREIGN PATENT DOCUMENTS

| | | |
|---|---|---|
| EP | 1275342 A2 | 1/2003 |
| WO | 2004030535 A1 | 4/2004 |
| WO | 2004057704 A1 | 7/2004 |
| WO | 2004084985 A1 | 10/2004 |

* cited by examiner

*Primary Examiner* — Lee Cohen (57) ABSTRACT

An electrode assembly is provided. The electrode assembly is arranged for receiving a connector. The electrode assembly includes a first electrode, a second electrode, and a bridge member extending between the first and second electrodes. The bridge member includes a first conductive trace extending from the first electrode, and a second conductive trace extending from the second electrode.

19 Claims, 8 Drawing Sheets

MULTI-CONDUCTOR CONNECTION DEVICE FOR A MEDICAL SENSOR

CROSS REFERENCE TO RELATED APPLICATIONS

This application claims the benefit of U.S. provisional application Ser. No. 60/648,819 filed Jan. 31, 2005, which is incorporated herein by reference.

The following relates to patient monitoring. It finds particular application in impedance cardiography and will be described with particular reference thereto.

The study of the performance and properties of the cardiovascular system of a living subject can be useful for diagnosing and assessing any number of conditions or diseases within the subject. The performance of the cardiovascular system, including the heart, has characteristically been measured in terms of several output parameters, including the stroke volume and cardiac output of the heart.

Impedance cardiography (ICG), also known as thoracic electrical bioimpedance (TEB), is a technology that measures changes in thoracic impedance and relates them to such stroke volume and cardiac output parameters of the heart. In this manner, ICG is used to track volumetric changes such as those occurring during the cardiac cycle. These measurements, which are gathered noninvasively and continuously, have become more sophisticated and more accurate with the development of data signal processing and improved mathematical algorithms.

More strictly speaking, impedance cardiography is used to measure the stroke volume of the heart and heart rate. As shown in Eq. (1), when the stroke volume is multiplied by heart rate, cardiac output (CO) is obtained.

$$CO = \text{Stroke Volume} \times \text{Heart Rate} \quad (1)$$

During impedance cardiography, a constant alternating current, with a frequency such as 70 kHz is applied across the thorax. The resulting voltage is used to calculate impedance. The calculated impedance is then used to calculate stroke volume in accordance with known calculations.

A basic method of correlating thoracic, or chest cavity, impedance, $Z_T(t)$, with stroke volume generally includes modeling the thoracic impedance $Z_T(t)$ as a constant impedance, $Z_o$ and a time-varying impedance, $\Delta Z(t)$. The time-varying impedance is measured by way of an impedance waveform derived from electrodes placed on various locations of the subject's thorax; changes in the impedance over time can then be related to the change in fluid volume (i.e., stroke volume), and ultimately cardiac output via Equation (1) above.

The method described above used continuous electrode bands around the neck and lower thorax. In an effort to increase comfort and utility, standard ECG electrodes have subsequently been used. With ECG electrodes, proper diagnosis depended on the user's knowledge and care in placing these electrodes properly. Such placement involves placing two electrodes at each of the following general locations: right side of the neck, left side of the neck, right side of the thorax, and left side of thorax, for a total of eight electrodes.

Despite their general utility, the previous impedance cardiography techniques suffered from certain disabilities. First, the distance (and orientation) between the terminals of the electrodes which are placed on the skin of the subject can be variable; this variability can introduce error into the impedance measurements. Specifically, individual electrodes which typically include a button snap-type connector, compliant substrate, and gel electrolyte, are affixed to the skin of the subject at locations determined by the user. Since there has been no direct physical coupling between the individual electrodes, their placement has been somewhat arbitrary, both with respect to the subject and with respect to each other. Hence, two measurements of the same subject by the same user could produce different results, dependent at least in part on the user's choice of placement location for the electrodes. It has further been shown that with respect to impedance cardiography measurements, certain values of electrode spacing yield better results than other values.

In light of the foregoing, recent ICG electrodes have included two electrodes mounted a given distance, such as 5 cm, apart on a common substrate. These electrode pairs can be convenient, simple and reliable.

However, connecting eight different cable leads from the ICG monitor to the eight electrodes on the subject is still done on an individual basis in some cases. This process can be time-consuming. Further, each pair of two electrodes at each location on the subject includes one drive electrode and one sense electrode. The drive electrode is used for providing a signal to the subject and the sense electrode is used for sensing a signal from the subject. Due to such an arrangement, errors can be made while connecting the cables to the electrodes wherein a drive lead may be attached to a sense electrode and vice versa.

In light of the above, another connection scheme which is used is a double connector. Such double connector includes a rigid housing in which a drive lead and sense lead are arranged. The housing then attaches as a unit to a pair of electrodes. This scheme offers the advantage that it appears to the user as if only four electrodes and four cables are required. Here, application is simpler, faster, and less obtrusive than in the case which requires eight individual connections. The scheme, however, has the disadvantage of increased stiffness between the electrodes. This makes the electrodes less likely to remain in good electrical contact with the patient. It also makes it difficult to apply the connector in some cases.

Additionally, as the subject moves, contorts, and/or breathes during ICG protocols, the relative orientation and position of the individual electrodes may vary. Electrodes may also be displaced laterally to a different location on the skin through subject movement, tension on the electrical leads connected to the electrodes, or even incidental contact. This so-called "motion artifact" can also reflect itself as reduced accuracy of the cardiac output measurements obtained using the impedance cardiography device.

Based on the foregoing, there is a need for an improved apparatus and method for measuring cardiac output in a subject. The present invention contemplates an improved apparatus and method that overcomes the aforementioned limitations and others.

In accordance with one aspect of the invention, an electrode assembly arranged for receiving a connector is provided. The electrode assembly includes a first electrode, a second electrode, and a bridge member extending between the first and second electrodes. The bridge member includes a first conductive trace extending from the first electrode, and a second conductive trace extending from the second electrode.

In accordance with another aspect of the invention, a subject monitoring apparatus is provided. The apparatus includes a drive unit (10), a sense unit (50), a plurality of electrode assemblies disposed on the subject, each electrode assembly including a drive electrode, a sense electrode, a bridge member extending between the drive and sense electrodes, a first conductive trace extending from the drive electrode along the bridge member, and a second conductive trace extending from the sense electrode along the bridge member.

One advantage of an embodiment of the invention is that a reduction in the number of mechanical connections for connecting ICG cables to ICG electrodes is facilitated.

Another advantage of an embodiment of the invention is that the flexibility of an electrode assembly is facilitated.

Another advantageous of an embodiment of the invention is that a plurality of orientations and positions of a connector with respect to an electrode assembly is facilitated.

Another advantage of an embodiment of the invention is that reduction in errors related to electrical connections between electrodes and cables is facilitated.

Another advantage of an embodiment of the invention is that a reduction in attachment/detachment forces transmitted to the subject is facilitated.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 1:
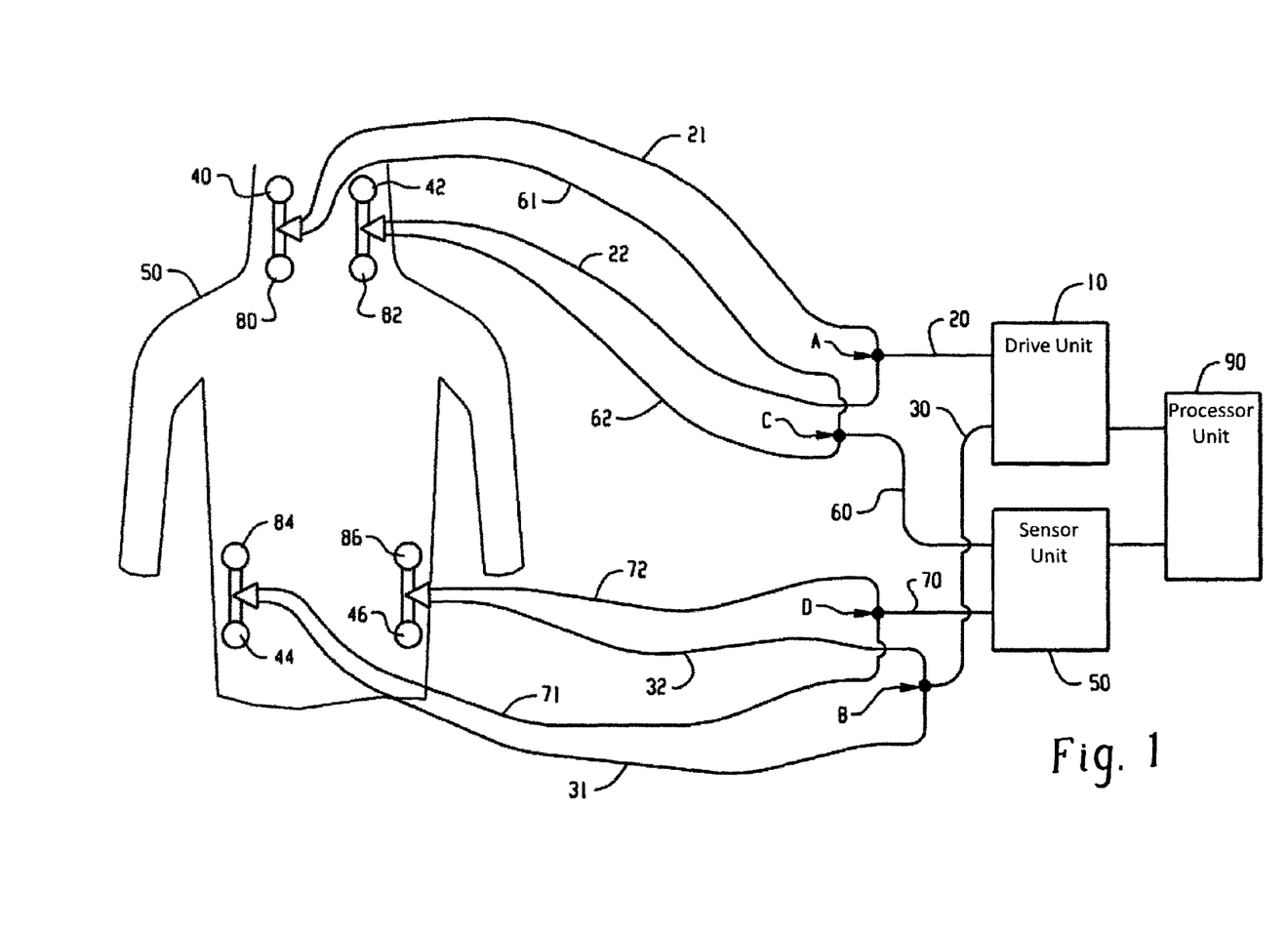
FIG. 1 shows a diagrammatic illustration of an impedance cardiography system.

With reference to FIG. 1, an embodiment of an impedance cardiography (ICG) system is shown. The ICG system includes a drive unit 10, first and second drive cables 20, 30 and first, second, third, and fourth drive electrodes 40, 42, 44, 46. The first and second drive electrodes 40, 42 are positioned in approximately equal superior/inferior positions on the right and left sides, respectively, of the neck of a subject 50 and are electrically connected to the drive unit 10 via the first drive cable 20. More specifically, the first drive cable 20 is divided into two branches at point A. The first branch 21 of the first drive cable is connected to the first drive electrode 40 and the second branch 22 of the first drive cable is connected to the second drive electrode 42.

The third and fourth drive electrodes 44, 46 are positioned in approximately equal superior/inferior positions on the right and left sides, respectively, of the thorax of the subject 50 and are electrically connected to the drive unit 10 via the second drive cable 30. More specifically, the second drive cable 30 is divided into two branches at point B. The first branch 31 of the second drive cable is connected to the third drive electrode 44 and the second branch 32 of the second drive cable is connected to the fourth drive electrode 46.

The ICG system also includes a sensor unit 50, first and second sensor cables 60, 70 and first, second, third, and fourth sensor electrodes 80, 82, 84, 86. The first and second sensor electrodes 80, 82 are positioned in approximately equal superior/inferior positions on the right and left sides, respectively, of the neck of a subject 50 and are electrically connected to the sensor unit 50 via the first sensor cable 60. With respect to the first and second drive electrodes 40, 42, the first and second sensor electrodes 80, 82 are positioned a given distance L in an inferior direction. Further, the first sensor cable 60 is divided into two branches at point C. The first branch 61 of the first sensor cable is connected to the first sensor electrode 80 and the second branch 62 of the first sensor cable is connected to the second sensor electrode 82.

The third and fourth sensor electrodes 84, 86 are positioned in approximately equal superior/inferior positions on the right and left sides, respectively, of the thorax of the subject 50 (approximately at the height of the xiphoid process) and are electrically connected to the sensor unit 50 via the second drive cable 70. With respect to the third and fourth drive electrodes 44, 46, the third and fourth sensor electrodes 84, 86 are positioned a given distance L in a superior direction. Further, the second drive cable 70 is divided into two branches at point D. The first branch 71 of the second sensor cable is connected to the third sensor electrode 84 and the second branch 72 of the second sensor cable is connected to the fourth sensor electrode 86.

Figure 2:
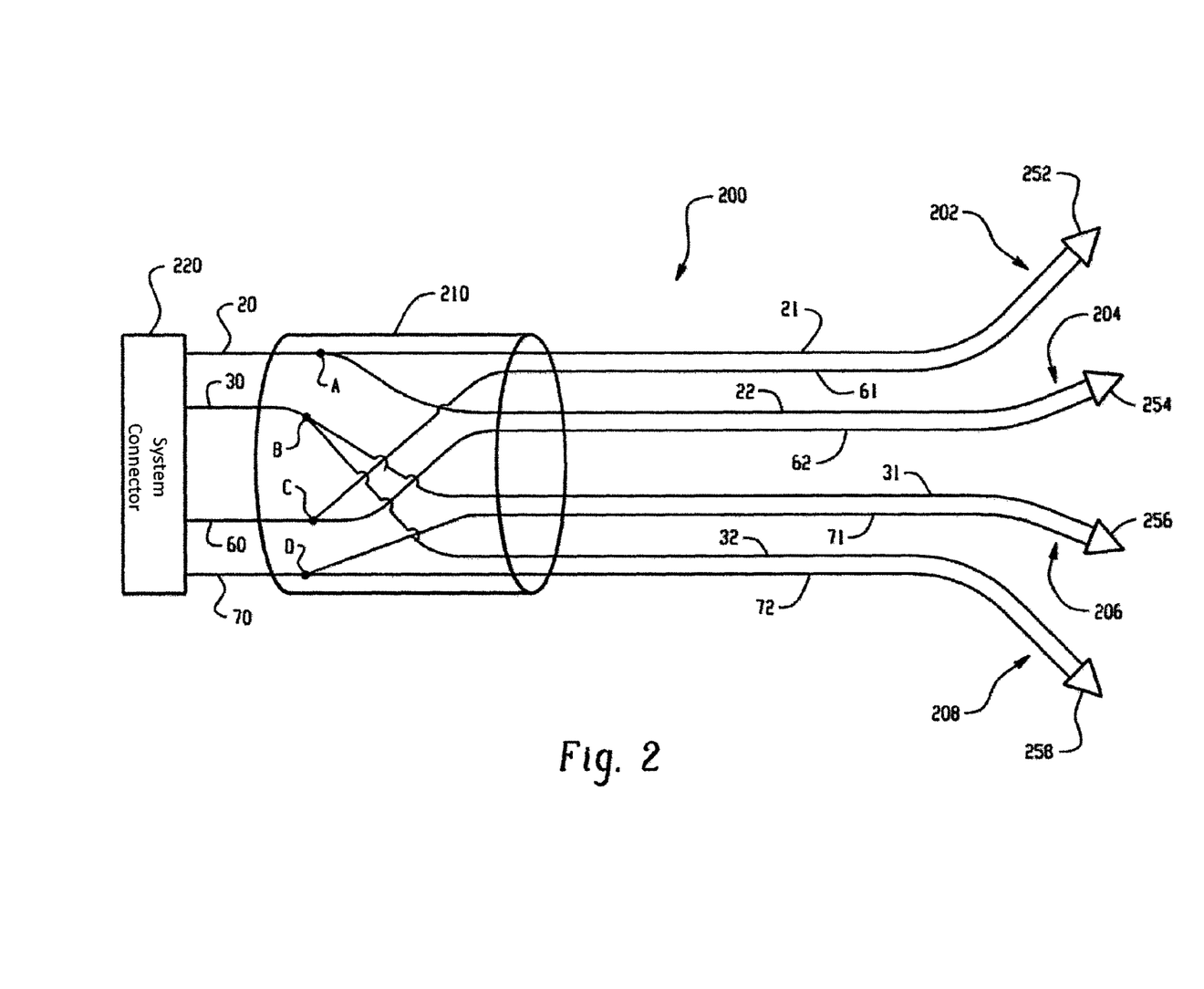
FIG. 2 shows a cable assembly for use in connection with an ICG system.

While FIG. 1 shows various drive and sensor cables, it is to be understood that the illustrated cables can be packaged into a cable assembly 200 as shown in FIG. 2. FIG. 2 shows that the cable assembly 200 includes a system connector 220, a yoke 210, which along with the drive and sense cables which span between them make up a trunk cable, and first 202, second 204, third 206 and fourth 208 pairs of cable branches. The first pair 202 of cable branches includes the first branch 21 of the first drive cable and the first branch 61 of the first sense cable. Analogously, each of the remaining pairs of cable branches 204, 206, 208, each include a drive cable branch and a sense cable branch as shown in FIG. 2. In one embodiment, each branch includes a co-axial cable. In the embodiment shown, the cable branches pass through the yoke where they are appropriately routed to respective drive and sense cables. The drive and sense cables are then routed to the system connector which can be connected to a given monitor. It is to be understood that each pair of cable branches can be inserted and removed from the yoke via cable receptacles on the yoke and connectors on the cable pairs.

Continuing with FIG. 2, the cable assembly 200 also includes first 252, second 254, third 256, and fourth 258 connectors at respective terminal ends of the pairs of cable branches. As will be described more fully below, each connector makes connection with an electrode assembly. For example, the first connector 252 connects the drive 40 and sense 80 electrodes disposed on the right side of the subject's neck to the first branches of the first drive and first sense cables, respectively.

The drive unit and sensor unit are connected to a processing unit 90 which processes signals received from the drive and sensor units.

Figure 3A:
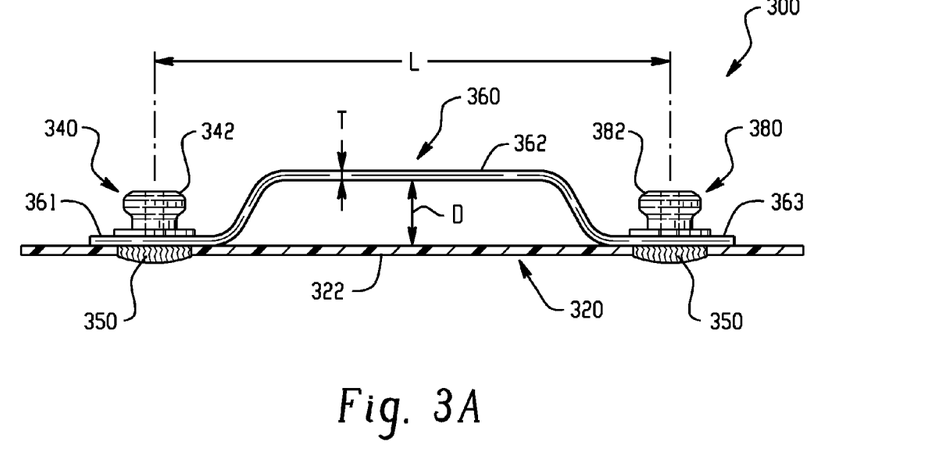
FIG. 3A shows a front view of an illustration of an electrode assembly.
Figure 3B:
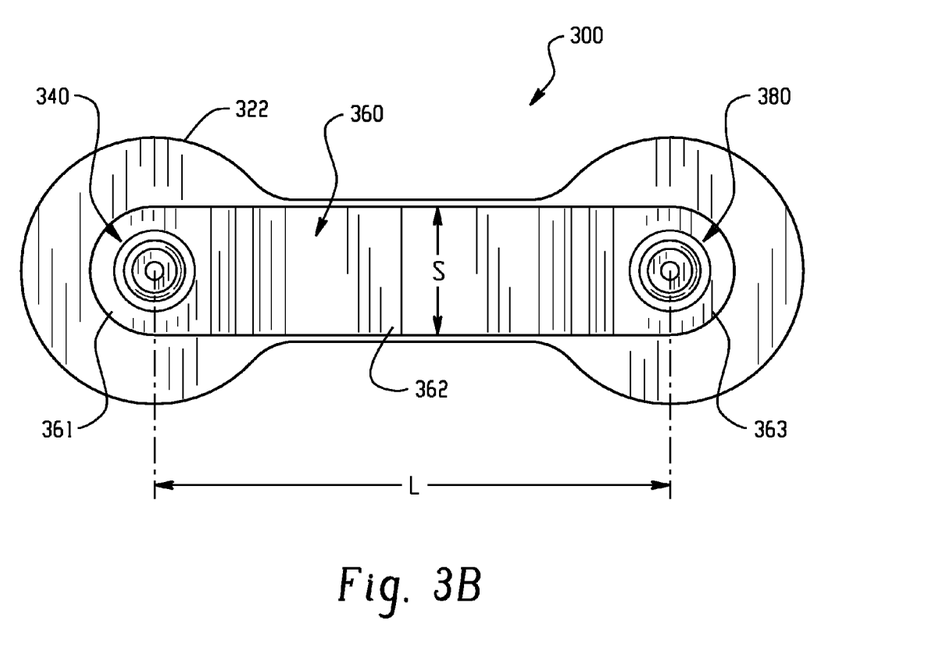
FIG. 3B shows a top view of an electrode assembly.

Turning to FIGS. 3A-3C, an embodiment of an electrode assembly 300 is shown. For the purposes of explanation, the electrode assembly will be described in connection with one pair of electrodes, it is to be understood, however, that the description can apply to each pair of electrodes disposed on the subject.

In the embodiment shown, the electrode assembly 300 includes a first electrode 340 and a second electrode 380. In one embodiment, the first electrode is a drive electrode and the second electrode is a sense electrode. The electrode assembly includes a base portion 320 which includes a flexible substrate 322, such as a foam, and adhesive so that the electrode assembly can be attached to the skin of the subject. The electrode assembly also includes gel electrolyte (or other electrically-conductive material) 350 to facilitate electrical connection between the subject and the ICG system.

In the embodiment shown, each electrode 340, 380 includes a male snap portion 342, 382 which protrudes from the base portion 320 as shown in FIG. 3A. Bridging the drive 340 and sense 380 electrodes is a bridge member 360.

In the embodiment shown in FIGS. 3A and 3B, first and second ends 361, 363 of the bridge member are secured between the male snap portions of the electrodes 340, 380 and the base portion 320 of the electrode assembly 300 such that they are in electrical contact with the electrolyte gel under their respective electrodes. An arch member 362 spans from the first end of the bridge member to the second end of the bridge member. As shown in the embodiment of FIG. 3A, the arch member is disposed from the base portion 320 of the electrode assembly, thereby providing a space D in its central portion.

Figure 4A:
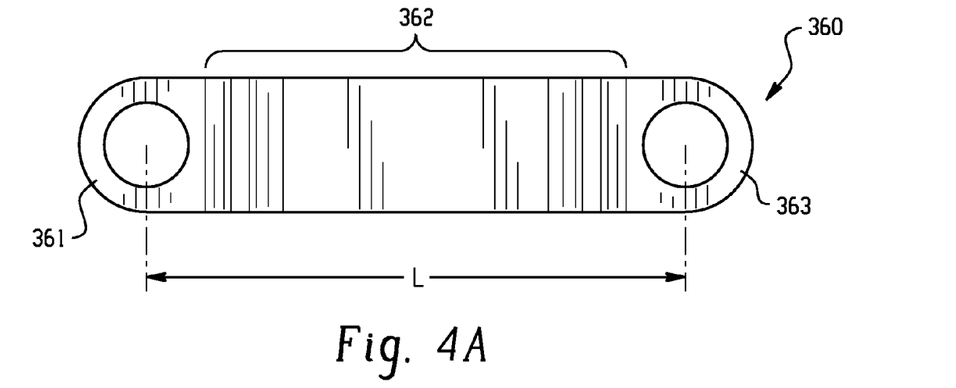
FIG. 4A shows a top view of a bridge member.
Figure 4B:
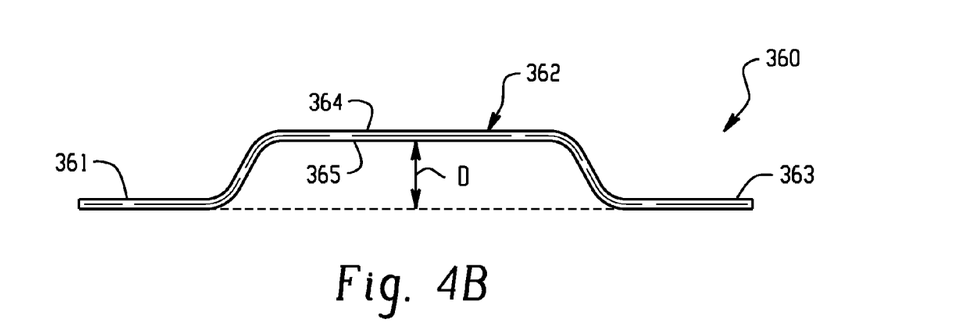
FIG. 4B shows a front view of a bridge member.
Figure 4C:
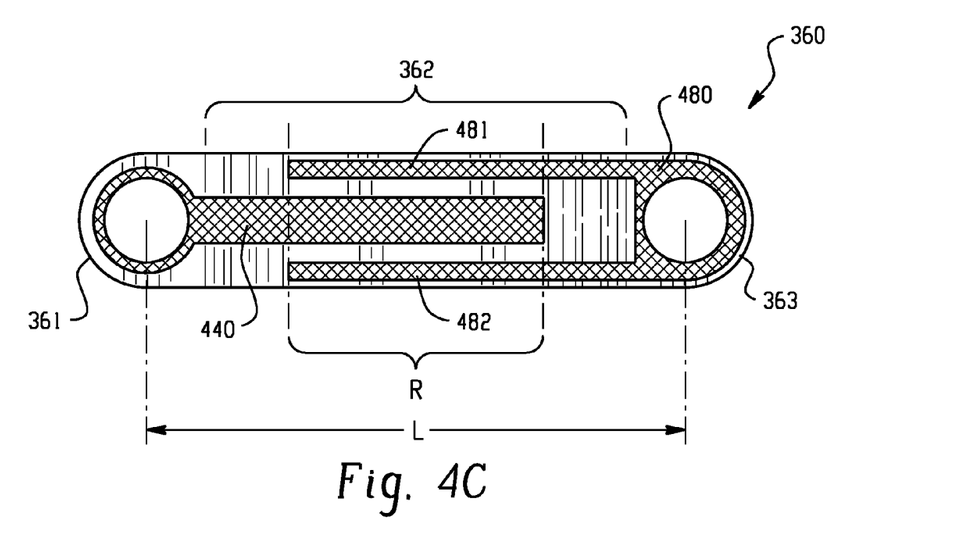
FIG. 4C shows a bottom view of a bridge member.

Turning to FIGS. 4A-4C, the bridge member 360 is shown in greater detail. As shown in FIG. 4A, from a top view perspective, the bridge member includes an elongated member which extends at least the length L. As shown in FIG. 4B, the bridge member 360 includes an upper surface 364 and a lower surface 365 and a thickness T.

With respect to FIG. 4C, the bridge member also includes first 440 and second 480 conductive traces disposed on the lower surface 365 of the bridge member. As shown in this embodiment, the first conductive trace 440 extends from the first end 361 of the bridge member along a central portion of the bridge member to the arch member 362. The second conductive trace 480 extends from the second end 363. The second conductive trace diverges into first and second trace branches 481, 482 which extend proximate to the periphery of the bridge member. The first and second trace branches extend to the arch member. In the embodiment shown in FIG. 4C, the first and second conductive traces 440, 480 extend over the arch portion 362 in a common region R and are electrically isolated from one another.

In one embodiment, the bridge member is fabricated out of flexible material such as polyimide. The conductive traces can be made from silver or copper adhered to the polyimide as a foil, or electrodeposited and etched, or by conductive ink.

Figure 5A:
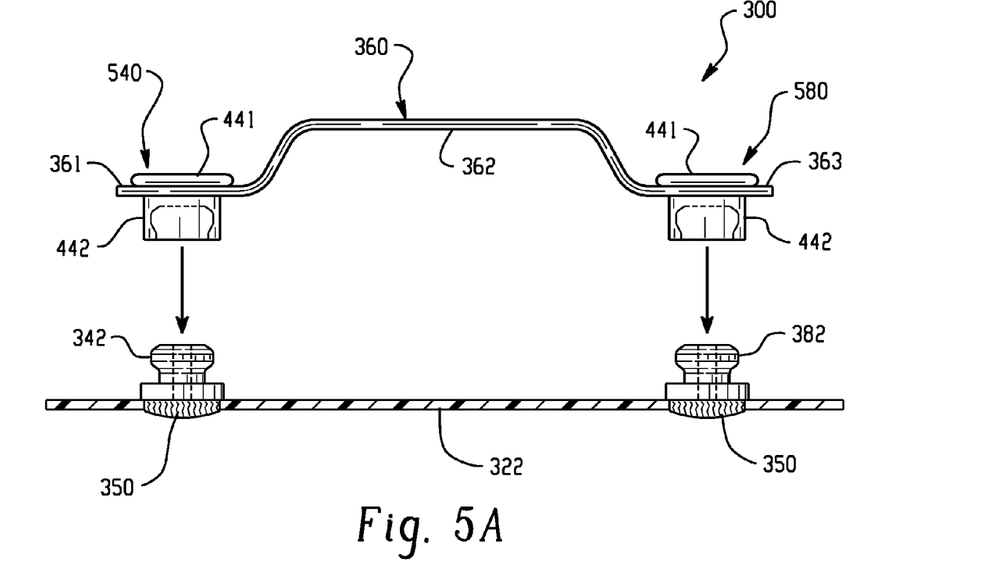
FIG. 5A shows a front view of a bridge member and an electrode pair.
Figure 5B:
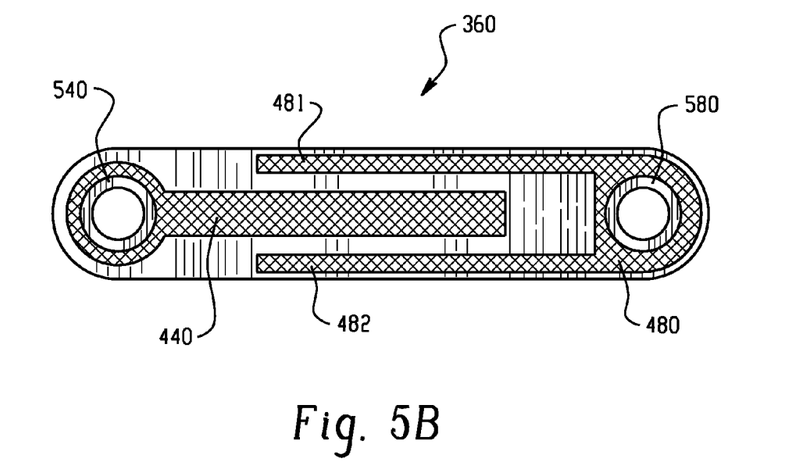
FIG. 5B shows a bottom view of a bridge member.

Another embodiment of an electrode assembly 300 is shown in FIGS. 5A and 5B. In this embodiment, the bridge member 360 includes first and second female snap members 540, 580. In this embodiment, the bridge member is secured by fastening the female snap members to respective male snap members 342, 382. With respect to FIG. 5B, the bridge member also includes first 440 and second 480 conductive traces disposed on the lower surface of the bridge member. As shown in this embodiment, the first conductive trace 440 extends from the first end 361 of the bridge member along a central portion of the bridge member to the arch member 362. The second conductive trace 480 extends from the second end 363. The second conductive trace diverges into first and second trace branches 481, 482 which extend proximate to the periphery of the bridge member. The first and second trace branches extend to the arch member. In the embodiment shown in FIG. 5B, the first and second conductive traces 440, 480 extend over the arch portion 362 in a common region R and are electrically isolated from one another.

Each female snap assembly 540, 580 includes an inner portion, a socket 442, and an outer portion, a button 441. Both portions can be made of stainless steel. During assembly, the shank of the button is pushed through a hole in the bridge member, including a hole in the trace, and then through a hole in the socket. The assembly is secured by a press operation, wherein a punch expands the shank of the button so the parts remain tightly assembled, forming a mechanical assembly and an electrically conductive path.

Turning to FIGS. 6A-6D, a connector 600 is shown. The connector 600 is an embodiment of the first, second, third, and fourth connectors 252, 254, 256, 258 disposed at the terminal ends of the pairs of cable branches of the cable assembly 200. In the embodiment shown, the connector 600 is a spring-loaded clothespin-like device. As shown, the connector includes a base housing 610, or lower jaw member and an upper jaw member 620 which is coupled to the lower jaw member by a pivot member 630. In one embodiment, the pivot member 630 includes a spring loaded pivot joint. Here, the pivot connects the lower jaw and the upper jaw with the spring in-between, and permits relative rotation between the jaws. The base housing, upper jaw, and pivot member can be formed of injection molded plastic.

The base housing 610 includes a channel 612, having width W. First and second electrical contacts 640, 680 are disposed within the channel. The first electrical contact 640 is disposed in a central region of the channel and the second electrical contact is disposed in a peripheral region of the channel. The contacts can be secured in the base by insert-molding or by trapping them between plastic parts.

Figure 6A:
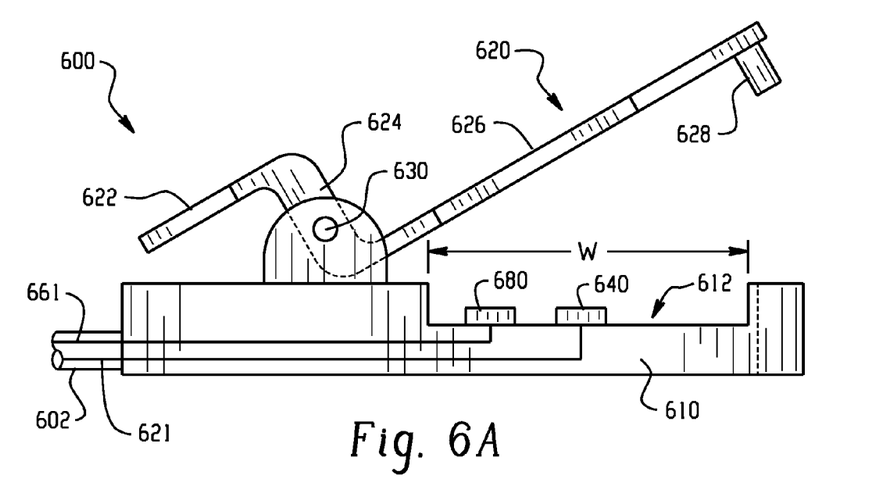
FIG. 6A shows a side view of a connector.

As can be seen in FIG. 6A, the base housing is coupled to a terminal end of a cable 602. The cable 602 includes first 621 and second 661 cables, or cable branches. In the embodiment shown, the first cable 621 is coupled to the first electrical contact 640 and the second cable 661 is coupled to the second electrical contact. Accordingly, in connection with the cable assembly 200, the cable 602 can be a pair of cable branches as shown in FIG. 2, the first and second cables 621, 661 can be drive and sense cable branches, and the electrical contacts 640, 680 can be drive and sense electrical contacts.

Figure 6B:
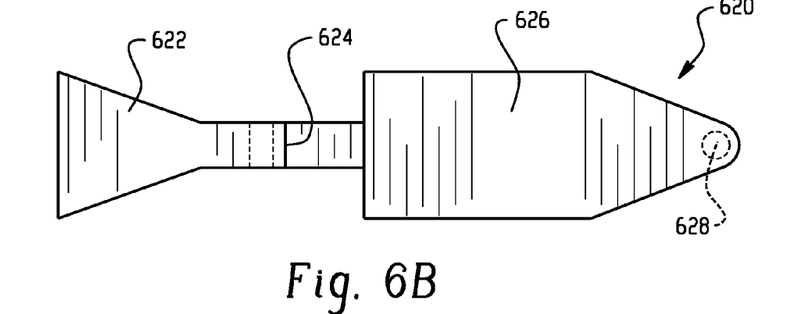
FIG. 6B shows a top view of an upper jaw of a connector.
Figure 6C:
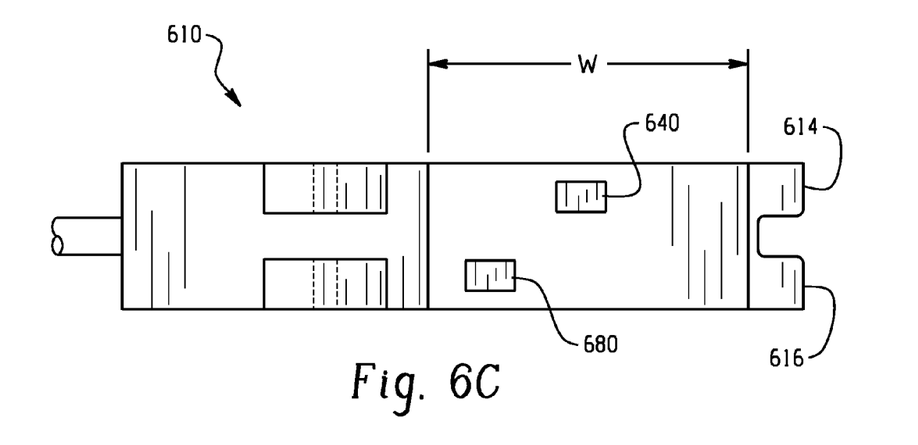
FIG. 6C shows a top view of a lower jaw of a connector.
Figure 6D:
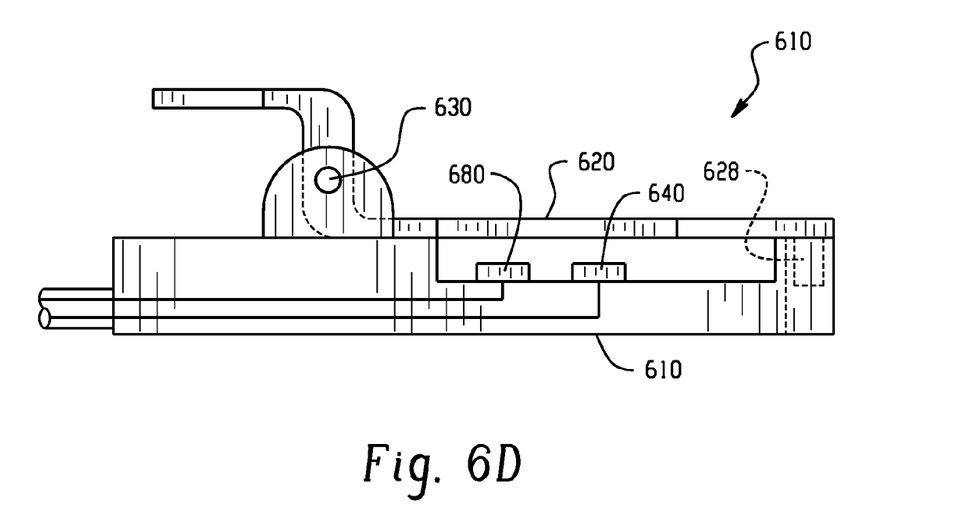
FIG. 6D shows a connector in a closed position.

Turning to FIG. 6B, the upper jaw portion 620 includes a handle portion 622, a hinge portion 624, a clamping portion 626, a pin 628 disposed at the tip of the upper jaw. The upper jaw portion is coupled to the base, at its hinge portion 624 via pivot joint 630. In one embodiment, the pivot joint is spring loaded. As shown in FIG. 6D, in a closed position, the clamping portion of the upper jaw portion is held against the base housing by spring forces in the pivot joint. In this closed position, the pin 628 is disposed between first and second end portions 614, 616 of the base housing for providing stability and proper alignment to the connector. In this embodiment, the channel in the base housing has a height H.

When used in connection with an electrode assembly as described above, the width W of the channel is slightly larger than the width S of the bridge member 360 and the height of the channel is approximately equal to the thickness T of the bridge member.

Figure 7:
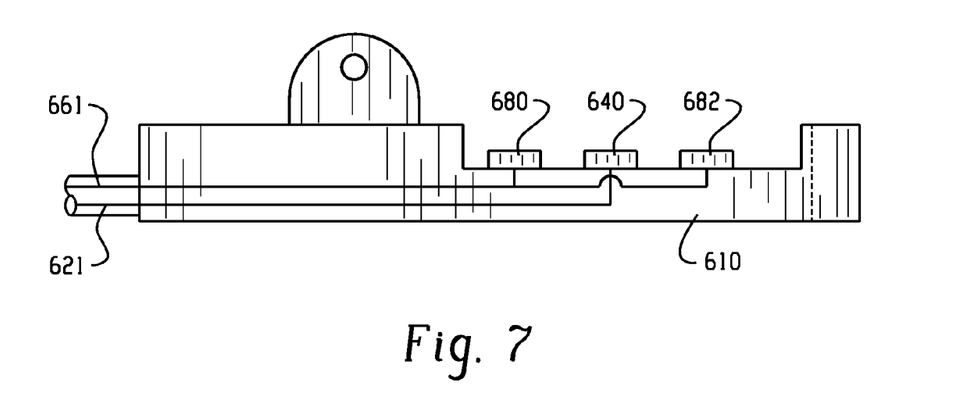
FIG. 7 shows a side view of a lower jaw of a connector with three electrical contacts.
Figure 8A:
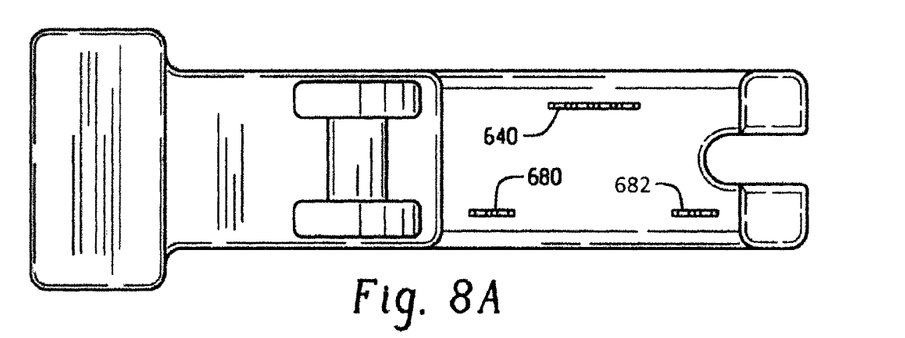
FIG. 8A shows a top view of a lower jaw of a connector.
Figure 8B:
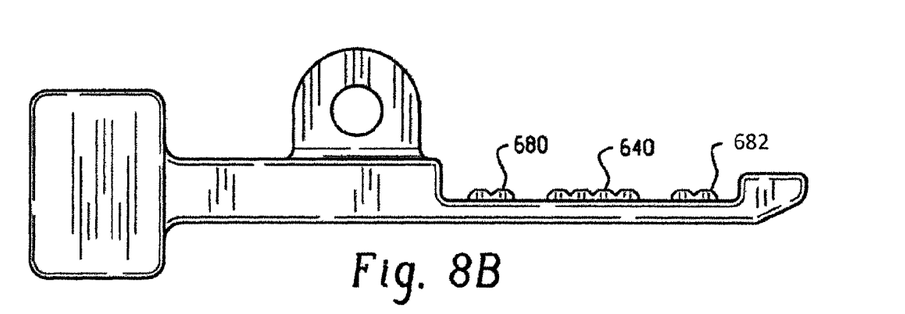
FIG. 8B shows a side view of a lower jaw of a connector.
Figure 8C:
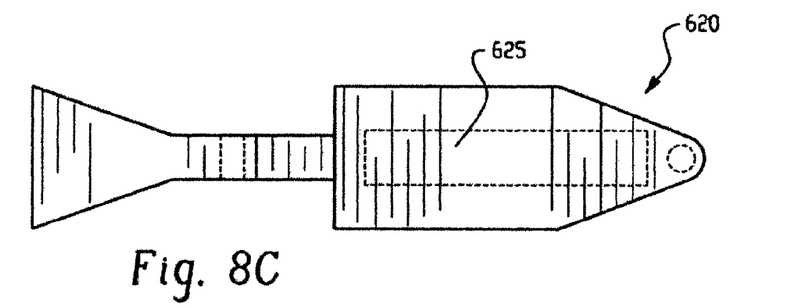
FIG. 8C shows a top view of an upper jaw of a connector.
Figure 8D:
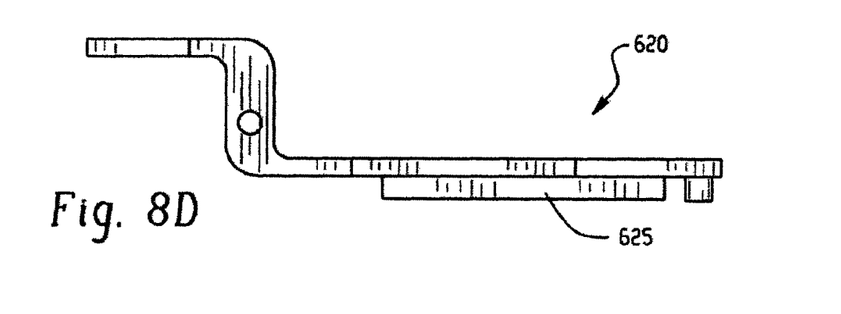
FIG. 8D shows a side view of an upper jaw of a connector.

In another embodiment, shown in FIG. 7, the base housing includes a third electrical contact 682 disposed along the periphery of the channel 612, opposite the second electrical contact 680. As with the second contact 680, the third contact 682 is in electrical contact with the second cable 661. The contacts are shown as rectangular solids, but may be bifurcated or serrated as shown in FIGS. 8A and 8B. With respect to the upper jaw, in the embodiment shown in FIGS. 8C and 8D, the upper jaw includes a protrusion 625 which passes along a mid-line of the upper jaw from an area corresponding to the second electrical contact to an area corresponding to the third contact. In operation, the protrusion facilitates electrical contract between the conductive traces of the electrode assembly and the electrical contacts of the connector.

In operation according to one embodiment of the invention, four electrode assemblies 300 are disposed on the subject, one pair at each of the following locations: right neck, left neck, right thorax, and left thorax. The orientation of the electrode assemblies disposed on the neck is such that the drive electrode is superior to the sense electrode. The orientation of the electrode assemblies on the thorax is such that the drive electrode is inferior to the sense electrode. In one embodiment, the drive electrode is the first electrode 340 of the electrode assembly and the sense electrode is the second electrode 380 of the electrode assembly.

Cable connectors 600 are then connected to the electrode assemblies. For example, the first connector 252 which is disposed at the end of the first pair of cable branches 202 is connected to the electrode assembly which includes first drive 40 and sense 80 electrodes. In order to make the connection to the electrode assembly, pressure is applied to the handle 622 of the upper jaw to open the jaws 610, 620 of the connector. The lower jaw 610 is passed under the bridge member 360 of the connector pair and the upper jaw 620 is passed over the bridge member. Once the connector is in a desired position, e.g. when the arch 362 of the bridge portion is disposed in the channel of the lower jaw, the pressure on the handle is released and the spring joint 630 holds the connector to the bridge unit by clamping the bridge unit between the clamping portion 626 and the lower jaw 610. In light of this connection, forces applied to the subject are minimal during the connection process.

In accordance with the above mechanical connection, electrical connection between drive and sense cables is made with drive and sense electrodes. More specifically, the first conductive trace 440 disposed on the lower surface of the bridge member comes into electrical contact with the first electrical contact 640 disposed in the channel of the lower jaw. The first branch 21 of the first drive cable is thus connected to the first drive electrode. Likewise, if the connector is applied to the bridge member from a first direction (e.g. from a posterior direction in the case of the electrode assembly disposed on the right side of the subject's neck), the first branch 481 of the second conductive trace 480 comes into electrical contact with the second electrical contact 680 disposed in the channel of the lower jaw. In the case where there is a third electrical contact 682 in the channel of the lower jaw, electrical connection is made between the third electrical contact and the second branch of the second conductive trace 482. In the case where the connector is applied from a second direction (e.g. an anterior direction) the second branch 482 of the second conductive trace comes into contact with the second electrical contact 680 of the connector. If there is a third electrical contract 682, the first branch 481 of the second conductive trace comes into contact with the third electrical contact. The first branch 61 of the first sense cable is thus connected to the first sense electrode. Due to the nature of this arrangement and to the extent of common region R over which the conductive traces 440, 480 extend, it is to be understood that the connector can be applied to the bridge member in various positions and orientations while still making the necessary electrical contacts.

The above description in connection with the electrode assembly disposed on the right side of the subject's neck can be applied analogously to the other three electrode assemblies disposed on the subject. Further, while the electrode assembly and connector has been described with the drive and sense electrodes being the first and second electrodes 340, 380, respectively, it is to be understood that the electrodes of the electrode assembly are interchangeable, so long as the connector and associated drive and sense cables are arranged in accordance with the electrode assembly. To further ensure proper connections, electrodes assemblies can be marked so that it is clear to the user which electrode is the drive electrode and which is the sense electrode. Also, the pairs of cable branches and/or the connectors can be marked to designate whether the connector should attach to an electrode assembly on the neck or on the thorax.

Once the necessary connections have been made, the drive unit 10 provides, for example, a drive voltage or current, via the drive cables to the drive electrodes 40, 42, 44, 46. In one embodiment, a constant alternating current, with a frequency such as 70 kHz is applied to the drive electrodes. A resulting voltage is then measured using the sensor electrodes 80, 82, 84, 86. The voltage signals are taken from the sensors via respective sensor cables to the sensor unit 50.

Information related to the drive signal is sent from the drive unit to the processing unit 90. Also, the measured, or sensed, signals are sent from the sensor unit to the processing unit. The processing unit then uses the drive signal information and the received signals to calculate impedance. The calculated impedance is then used to calculate stroke volume, and cardiac output, in accordance with known calculations.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. An electrode assembly arranged for receiving a connector, the electrode assembly comprising:
   a first electrode;
   a second electrode; and
   a bridge member extending between the first and second electrodes, the bridge member including:
      a first conductive trace extending from the first electrode;
      a second conductive trace extending from the second electrode; and
      first and second snap portions disposed at first and second ends of the bridge member, the first and second snap portions coupled to the first and second electrodes, respectively.

2. The electrode assembly as set forth in claim 1, wherein the first conductive trace extends along a central region of the bridge member and the second conductive trace extends along a peripheral region of the bridge member.

3. The electrode assembly as set forth in claim 1, wherein the first and second electrodes are disposed on a substrate and the bridge member includes an arch member which is displaced at a distance from the substrate.

4. The electrode assembly as set forth in claim 3, wherein the first and second conductive traces extend along the arch member in a common region.

5. The electrode assembly as set forth in claim 1, wherein the first conductive trace extends along a central region of the bridge member and the second conductive trace includes first and second branches, the first branch extending along a first peripheral region of the bridge member and the second branch extending along a second peripheral region of the bridge member, opposite the first peripheral region.

6. The electrode assembly as set forth in claim 5, wherein the first and second conductive traces are disposed on the bridge member such that the connector can be connected to the electrode assembly in a plurality of orientations with respect to the electrode assembly while making similar electrical connections in each orientation.

7. The electrode assembly as set forth in claim 6, wherein the first electrode is a drive electrode and the second electrode is a sense electrode.

8. An electrode assembly arranged for receiving a connector, the electrode assembly comprising:
a first electrode;
a second electrode; and
a bridge member disposed between the first and second electrodes, the bridge member including:
 a first conductive trace extending from the first electrode, the first conductive trace extending along a central region of the bridge member; and
 a second conductive trace extending from the second electrode, the second conductive trace including first and second branches, the first branch extending along a first peripheral region of the bridge member and the second branch extending along a second peripheral region of the bridge member, opposite the first peripheral region.

9. The electrode assembly as set forth in claim 8, wherein the first and second electrodes are disposed on a substrate and the bridge member includes an arch member which is displaced at a distance from the substrate.

10. The electrode assembly as set forth in claim 9, wherein the first and second conductive traces extend along the arch member in a common region.

11. The electrode assembly as set forth in claim 8, wherein the first and second conductive traces are disposed on the bridge member such that the connector can be connected to the electrode assembly in a plurality of orientations with respect to the electrode assembly while making similar electrical connections in each orientation.

12. The electrode assembly as set forth in claim 11, wherein the first electrode is a drive electrode and the second electrode is a sense electrode.

13. The electrode assembly as set forth in claim 8, wherein the bridge member further includes:
first and second snap portions disposed at first and second ends of the bridge member, the first and second snap portions coupled to the first and second electrodes, respectively.

14. A subject monitoring apparatus comprising:
a drive unit;
a sense unit;
a plurality of electrode assemblies adapted to be disposed on the subject, each electrode assembly including:
 a drive electrode;
 a sense electrode;
 a bridge member extending between the drive and sense electrodes;
 a first conductive trace extending from the drive electrode along a central region of the bridge member;
 a second conductive trace extending from the sense electrode along the bridge member, the second conductive trace including first and second branches, the first branch extending along a first peripheral region of the bridge member and the second branch extending along a second peripheral region of the bridge member, opposite the first peripheral region;
a main cable for providing electrical connection between the electrode assemblies and the drive and sense units, the main cable including:
 a plurality of pairs of cable branches; and
 a connector disposed at the end of each pair of cable branches, each connector including:
  a drive contact for electrically connecting a drive branch of the cable to the first conductive trace; and
  a sense contact for electrically connecting a sense branch of the cable to the second conductive trace.

15. The subject monitoring apparatus as set forth in claim 14, wherein the connector at each end of the pairs of cable branches can be applied to its respective electrode assembly in a plurality of positions with respect to the electrode assembly while making the necessary electrical contacts in each position.

16. The subject monitoring apparatus as set forth in claim 14, wherein the drive and sense electrodes are disposed on a substrate and the bridge member includes an arch member between first and second ends of the bridge member, the arch member being disposed at a distance from the substrate.

17. A subject monitoring apparatus comprising:
a drive unit;
a sense unit;
a plurality of electrode assemblies adapted to be disposed on the subject, at least one of the electrode assemblies including:
 a drive electrode;
 a sense electrode;
 a bridge member extending between the drive and sense electrodes;
 a first conductive trace extending from the drive electrode along the bridge member;
 a second conductive trace extending from the sense electrode along the bridge member;
wherein the drive and sense electrodes are disposed on a substrate and the bridge member includes an arch member between first and second ends of the bridge member, the arch member being disposed at a distance from the substrate.

18. The subject monitoring apparatus as set forth in claim 17, further including:
a main cable for providing electrical connection between the electrode assemblies and the drive and sense units, the main cable including:
 a plurality of pairs of cable branches; and
 a connector disposed at the end of each pair of cable branches, each connector including:
  a drive contact for electrically connecting a drive branch of the cable to the first conductive trace; and
  a sense contact for electrically connecting a sense branch of the cable to the second conductive trace.

19. The subject monitoring apparatus as set forth in claim 18, wherein the connector at each end of the pairs of cable branches can be applied to its respective electrode assembly in a plurality of positions with respect to the electrode assembly while making the necessary electrical contacts in each position.

* * * * *